United States Patent
Strohmaier et al.

(12) 
(10) Patent No.: US 6,229,031 B1
(45) Date of Patent: May 8, 2001

(54) METHOD FOR MANUFACTURING RUMEN BYPASS FEED SUPPLEMENTS

(75) Inventors: George K Strohmaier, Medina, OH (US); Eiler D. Frederiksen, Henderson, NV (US)

(73) Assignee: Norel Aquisitions, Inc., Fairlawn, OH (US)

( * ) Notice: Subject to any disclaimer, the term of this patent is extended or adjusted under 35 U.S.C. 154(b) by 0 days.

(21) Appl. No.: 09/349,662

(22) Filed: Jul. 8, 1999

Related U.S. Application Data

(60) Provisional application No. 60/132,656, filed on May 5, 1999.

(51) Int. Cl.$^7$ .................................................. C07C 51/00
(52) U.S. Cl. ............................................................. 554/156
(58) Field of Search ................................................ 54/186

(56) References Cited

U.S. PATENT DOCUMENTS 5,234,701    8/1993   Cummings et al. .
5,382,678  * 1/1995   Vinci et al. ......................... 554/156
5,456,927   10/1995   Vinci et al. .

* cited by examiner

*Primary Examiner*—Deborah D. Carr
(74) *Attorney, Agent, or Firm*—Synnestvedt & Lechner LLP

(57) ABSTRACT

A method for the preparation of fatty acid calcium salt products in which an admixture is formed of reactive ingredients consisting of (a) a $C_{10}$–$C_{22}$ fatty acid mixture having greater than about 45 weight% of the $C_{10}$–$C_{22}$ fatty acid content in the form of fatty acid glycerides, and (b) from about 10 to about 30% of the total admixture weight of calcium oxide. Water is then added to the admixture in an amount between about 10% and about 100% by weight relative to the amount of calcium oxide; and the admixture is then heated to a temperature at which the fatty acid glycerides saponify to form fatty acid calcium salts. Rumen bypass feed supplements are also disclosed, as well as ruminant feeds containing the feed supplements and processes for supplying the feed supplements to ruminant animals.

9 Claims, No Drawings

METHOD FOR MANUFACTURING RUMEN BYPASS FEED SUPPLEMENTS

CROSS REFERENCE TO RELATED APPLICATION

The present patent application claims the priority benefit of a U.S. Provisional Patent Application Serial No. 60/132,656, filed on May 5, 1999. The disclosure of this application is incorporated herein by reference.

BACKGROUND OF THE INVENTION

The present invention relates to a process for the production of rumen bypass feed supplements that are useful as an energy source for ruminants. The process converts fatty acid glycerides or a mixture of fatty acid glycerides and free fatty acids to the respective calcium salts. The present invention also relates to processes in which animal and vegetable fats and oils and their by-products from the food industries such as meat-packing and restaurants, containing high amounts of glyceride or free fatty acids, are employed in the formation of fatty acid calcium salts.

Conventional cattle feeds such as corn and alfalfa often fail to provide sufficient energy for cattle, especially lactating dairy cattle during periods of heavy milk production and cattle in the last trimester before calving, when nutrient needs are increasing. Feed containing a high proportion of corn also has a tendency to depress the milkfat content of the milk produced by such cattle. Fat is an excellent energy source, and it is known that if the proportion of fat in cattle food is increased, lactating dairy cattle produce higher milk yields without draining their reserves of body fat and without diminishing the proportion of milkfat in the milk produced.

However, it has been found that if the proportion of fat in the diet of cattle exceeds about 2% of the total feed in solids, the feed has toxic effects upon the microorganisms in the rumen of the cattle. The rumen, the largest of the four stomach compartments of ruminants, is the site of digestive breakdown of ingested foodstuffs. Absorption by the animal, however, takes place further along in the alimentary tract, principally in the abomasum and intestines. Although the rumen endows the animal with the capacity to digest and utilize cellulose effectively, it is relatively inefficient in the digestion and utilization of dietary fats.

Furthermore, fats apparently reduce the growth rate or even kill the microorganisms that digest fiber in the rumen, thereby lowering cellulose digestibility. This deleterious effect on the rumen is particularly true of unsaturated fats. In addition to reducing the growth rate or killing cellulose-digesting microorganisms, triglycerides and free fatty acids can physically coat fibrous or cellulosic material in the rumen and thereby inhibit fermentation of the material by the bacteria. This has an adverse effect on the total digestibility of the diet, and can result in a reduced yield of milk and butterfat.

U.S. Pat. No. 4,642,317 describes the incorporation of insoluble fatty acid salts in ruminant feed as a means of increasing the fatty acid content without deleteriously affecting the ruminant digestion cycle. A feed additive such as a fatty acid calcium salt functions as a rumen bypass product, and is subsequently metabolized in the abomasum small intestine of the ruminant.

Producing fatty acid calcium salt products that are free-flowing granular powders is desirable, so that the product can be easily transported and used in feed rations. This physical form of a fatty acid calcium salt allows for the addition to the feed rations by simple blending with the remaining ingredients.

The critical properties required for a granular material to be free flowing are that it be tack-free, non-cohesive and have a low dust content. Otherwise, the product will tend to lump, agglomerate, and generate dust in the surrounding environment. The product should also experience minimal particle segregation that would result in a non-homogenous feed ration. It should also be stable from oxidative rancidity.

One way to obtain a free-flowing product is to employ a low glyceride content fatty acid feedstock. This is disclosed in U.S. Pat. No. 5,382,678. This requires intermediate and costly processing of fats and greases to reduce the glyceride content.

It would be preferable to directly produce free-flowing granular fatty acid calcium salt rumen bypass feed products from high glyceride content materials such as yellow grease, white grease, lard and tallow or other animal and vegetable fats and oils. These materials are relatively inexpensive byproducts of the food industry and restaurant trade. The aforementioned U.S. Pat. No. 5,382,678 discloses a process for producing low glyceride content fatty acid calcium salts in the form of tackless free-flowing granules by reacting a fatty acid mixture with a basic calcium compound in an aqueous suspension. However, a reduced glyceride content fatty acid distillate must be employed as the starting material.

There remains a need for a process by which fatty acid calcium salt rumen bypass feed supplements may be produced in free-flowing granular form from relatively inexpensive grease and fat byproducts.

SUMMARY OF THE INVENTION

This need is met by the present invention. It has now been discovered that freeflowing granular fatty acid calcium salts for use as rumen bypass feed supplements may be obtained by reacting high glyceride content fats and greases with calcium oxide and a minimal amount of water. Therefore, according to one aspect of the present invention, a method for the preparation of a fatty acid calcium salt product is provided in which an admixture is formed of reactive ingredients consisting of (a) a $C_{10}$–$C_{22}$ fatty acid mixture, having greater than about 45 weight% of the $C_{10}$–$C_{22}$ fatty acid content in the form of fatty acid glycerides; and (b) from about 10 to about 30% by total admixture weight of calcium oxide;

adding water to the admixture in an amount between about 10% and about 100% by weight relative to the amount of calcium oxide; and heating the admixture to a temperature at which the fatty acid glycerides saponify to form fatty acid calcium salts.

The process of the present invention obtains free-flowing fatty acid calcium salt granules from fat and grease byproducts with glyceride contents of up to 100%. The fats and greases are directly converted to the calcium salts without a fatty acid isolation intermediate process step. It is also not necessary to separate the glycerol resulting therefrom. The need to employ energy-intensive processes that diminish the economic viability of fatty acid calcium salt rumen bypass feed supplements is eliminated. The process also provides greater flexibility in the choice of fatty acid feedstocks, which represents an additional economic advantage.

Without being bound by any particular theory, it is believed that the glycerol that is generated complexes with the calcium hydroxide produced by the reaction between the calcium oxide and water, forming compounds such as calcium monoglycerolate, calcium diglycerolate, tricalcium octaglycerolate, calcium hexaglycerolate, as well as hydrated diglycerol salts such as $Ca(OH)_2.2C_3H_8O_3.H_2O$ or other hydroxide complexes such as $[Ca(C_3H_8O_3)_3](OH)_2$. It is believed that the glycerol that is generated complexes with the calcium hydroxide that is present as the admixture is dehydrated, resulting in a form of glycerol that does not interfere with the solidification and milling of the fatty acid calcium salt product into free-flowing granules. Therefore, according to another aspect of the present invention, a fatty acid calcium salt is provided, prepared by the method of the present invention.

The fatty acid distribution of the calcium salts of the present invention corresponds to the fatty acid distribution of the glyceride feedstocks. This can be advantageously utilized to obtain fatty acid distributions that are nutritionally beneficial. Ruminants fed with the fatty acid calcium salt products of the present invention exhibit improved body condition, milk production and reproductive function. The present invention thus also provides a process for supplying fatty acids to ruminant animals by feeding to the ruminant animals the fatty acid calcium salt product of the present invention in an amount equal to at least 1% of the dry matter content of the animal's feed. The present invention also includes a ruminant feed containing at least one vegetable material and at least 1% by weight on a dry solids basis of the fatty acid calcium salt product of the present invention.

The above and other objects, features and advantages of the present invention will become clear from the following description of the preferred embodiment.

DETAILED DESCRIPTION OF THE PREFERRED EMBODIMENT

The present invention provides a process by which animal and vegetable fats, oils, greases, grease by-products and other glyceride materials may be converted to free-flowing powder or granular fatty acid calcium salt rumen bypass feed supplements. The term "glyceride" as employed herein includes $C_{10}$–$C_{22}$ fatty acid monoglycerides, diglycerides and triglycerides, and any mixture thereof. These glyceride forms represent a significant departure from conventional processes for the manufacture of fatty acid calcium salt feed supplements.

The process of the present invention may be employed as either a batch or a continuous process. In a typical process according to the present invention, fatty acid glycerides, or a blend of fatty acid glycerides and free fatty acids, are added to a production vessel. The production vessel should be adapted to supply heat to the vessel contents, as well as to remove heat therefrom. The production vessel should also be adapted to mix the vessel contents under adequate shear to form a homogenous admixture of the vessel contents. Examples of reaction vessels suitable for use with the present invention include continuous or batch reactors, indirectly or directly heated, with multiple agitation and shear elements, suitable for very high viscosity materials. Typical examples are soap kettles.

The economic advantages provided by the process of the present invention are obtained when fatty acid feedstocks are employed having greater than about 45 weight% of the fatty acid content in the form of fatty acid glycerides. Typical fatty acid feedstocks range in fatty acid content between $C_{10}$ and $C_{22}$ fatty acids and fatty acid glycerides. The present invention is also operative with lower glyceride content fatty acid feedstocks, and with glyceride-free fatty acid feedstocks. However, the method of the present invention may be employed with fatty acid feedstocks in which from about 15% to about 100% by weight of the fatty acids are in glyceride form.

Preferred feedstocks include essentially any byproduct oil of animal or vegetable origin, including yellow grease, white grease, lard, tallow and any other glycerides with fatty acid profiles determined to be nutritionally beneficial to a ruminant. Glycerides with nutritionally beneficial fatty acid profiles are readily identified by those of ordinary skill in the art. Vegetable oils such as soybean oil, canola oil, sunflower oil, olive oil, corn oil, and the like, and byproducts thereof, as well as oils such as fish oils and byproducts thereof, may also be used.

Such fatty acid feedstocks typically contain from about 10 to about 100 weight% of the fatty acid content in the form of fatty acid glycerides, from about 0 to about 90% by weight of free fatty acids, and less than 5% by weight of moisture, insolubles and unsaponifiables. The free fatty acid content may be increased by adding fatty acid distillates to the feedstock.

Calcium oxide is added to the fatty acid feedstock in the range of from about 10 to about 30% by weight of the total composition. A calcium oxide level between about 12 and about 18% by weight of the total composition is preferred.

Water is then added to hydrate the calcium oxide to its hydroxide form, creating a large amount of exothermic heat. Additional heat is added to the admixture to increase the temperature to a range between about 90 and about 250° C. For lower levels of calcium oxide and lower levels of free fatty acids, higher temperatures should be employed. In accordance with the present invention, calcium hydroxide may be substituted for calcium oxide and a stoichiometric equivalent of water.

Lower reaction temperatures can be employed with higher levels of calcium oxide, and lower levels of calcium oxide can be employed with higher temperatures. Thus, an admixture containing 15 to 30% by weight of calcium oxide can be reacted at a temperature between about 90 and about 120° C., although the 15 to 20% by weight calcium oxide level should be used with fatty acid feedstock with glyceride contents between about 45 and about 75% by weight.

For reaction temperatures between about 120 and 250° C., calcium oxide levels between about 10% and about 15% by weight can be employed. A reaction temperature between about 180 and 220° C. is preferred. With 10% levels of calcium oxide, temperatures closer to 220–250° C. should be employed, or fatty acid feedstocks with glyceride contents between about 45 and about 75% by weight should be used. The proper amounts of calcium oxide and water, as well as the optimum temperature to employ, can be readily determined by those of ordinary skill in the art without undue experimentation.

The reaction can be performed under atmospheric pressure or at an elevated pressure to maintain the desired temperature. Between about 10% and about 100% by weight of water relative to the calcium oxide is added to the admixture. An amount between about 15 and about 40% by weight is preferred.

The amount of time required for the reaction is typically between about 10 to about 60 minutes, and more typically between about 15 and about 45 minutes. The reaction is easily identified by the transformation of the admixture into a caramel-like mass. Upon further heating and agitating, the mass further transforms into a taffy-like material, which, upon transfer from the reaction vessel, can easily be processed into free-flowing particles.

A biologically active material can be included as an optional ingredient in the invention process. By the term "biologically active material", it is meant any substance capable of being administered orally in a feed composition and which is susceptible to inactivation in the runen by microbes and digestive juices. The biologically active material can be selected from a broad variety of nutrients and medicaments, either as a single component or as a mixture of components, which are illustrated by the following list of active molecular species:

1. Sugars and complex carbohydrates which include both water-soluble and water-insoluble monosaccharides, disaccharides, and polysaccharides. Particularly preferred carbohydrates include cane molasses and sugar beet byproducts.

2. Amino acid ingredients, either singly or in combination, which include arginine, histidine, isoleucine, leucine, lysine, methionine, phenylalanine, threonine, tryptophan, valine, tyrosine ethyl HCL, alanine, aspartic acid, glutamic acid, sodium glutamate, potassium glutamate, glycine, proline, serine, cystine ethyl HCL, and the like; and analogues and salts thereof.

3. Vitamin ingredients, either singly or in combination, including thiamine HCL, riboflavin, pyridoxine HCL, niacin, inositol, choline chloride, calcium pantothenate, biotin, folic acid, ascorbic acid, vitamin $B_{12}$, p-aminobenzoic acid, vitamin A acetate, vitamin K, vitamin D, vitamin E, and the like.

4. Trace element ingredients, either singly or in combination, including compounds of cobalt, copper, manganese, iron, zinc, tin, nickel, chromium, molybdenum, iodine, chlorine, silicon, vanadium, selenium, calcium, magnesium, sodium and potassium.

5. Protein ingredients as obtained from sources such as dried blood or meat meal, meat and bone meal, cottonseed meal, soybean meal, rapeseed meal, sunflower seed meal, canola meal, safflower meal, dehydrated alfalfa, corn gluten meal, soybean protein concentrate, potato protein, dried and sterilized animal and poultry manure, fish meal, fish and poultry protein isolates, crab protein concentrate, hydrolyzed protein feather meal, poultry byproduct meal, liquid or powdered egg, milk whey, egg albumen, casein, fish solubles, cell cream, brewer's residues, and the like.

6. Medicament ingredients, either singly or in combination, including promazine hydrochloride, chloromedoniate acetate, chlorotetracycline, sulfamethazine, monensin, sodium monensin, poloxaline, oxytetracycline, BOVATEC, and the like.

7. Antioxidants, including butylated hydroxyanisole, butylated hydroxytoluene, tertiary-butylhydroquinone, tocopherols, propyl gallate and ethoxyquin; and preservatives, including sodium sorbate, potassium sorbate, sodium benzoate, propionic acid, α-hydroxybuteric acid, and the like.

The biologically active material is present at a level up to about 20 weight %, based on the weight of the $C_{10}$–$C_{22}$ fatty acid ingredient.

The fatty acid calcium salt rumen bypass feed supplements of the present invention may be conveniently fed to a ruminant admixed with a conventional ruminant feed. The feeds are typically vegetable materials edible by ruminants, such as legume hay, grass hay, corn silage, grass silage, legume silage, corn grain, oats, barley, distiller's grain, brewer's grain, soya bean meal and cottonseed meal. Desirably, the amount of the calcium salt supplement in such an admixture does not exceed about 10% of the dry solids content of the feed and is preferably about 3 to 5% of the dry solids content of the feed.

There is no particular lower limit for the amount of the calcium salt to be added to the ruminant feed, although in practice amounts of the calcium salt below about 1% of the dry solids content of the feed are too small to provide significant amounts of energy to the ruminant. It is known to feed small amounts of fatty acid mixtures to cattle only as an inert protective agent for certain feed supplements such as methionine, as is disclosed in U.S. Pat. No. 3,959,493. However, the amounts of fatty acids fed to cattle in this manner are much smaller than contemplated with the feed supplements of the present invention.

The calcium salts of the present invention are ideal nutritional supplements for cattle, particularly lactating dairy cattle, for which conventional cattle feeds, such as corn and alfalfa, often fail to provide sufficient energy, especially during periods of stress or heavy milk production. The feed supplements of the present invention contain elevated levels of calcium salts of long chained fatty acids and calcium salts of unsaturated fatty acids that improve energy utilization in cattle. Accordingly, the rumen bypass feed supplements of the present invention are particularly well suited for use as nutritional supplemental additives for cattle feeds.

The following non-limiting examples set forth hereinbelow illustrate certain aspects of the invention. All parts and percentages are by weight unless otherwise noted, and all temperatures are in degrees Celsius.

EXAMPLES

Example 1

Ingredients: 380 grams yellow grease 100 grams CaO 100 grams water

The yellow grease was heated to 70° C., and the CaO was added and thoroughly mixed. The yellow grease had a free fatty acid concentration from about 5 to about 15%. The water was added to the mixture and allowed to hydrate the CaO in a sealed pressure vessel. When the hydration was complete, the temperature was increased to 150° C., with mixing. Ten minutes later, the mixture was cooled to below 100° C. and the pressure vessel was opened to permit drying of the water that was released from the mixture. When the mixture's moisture was below about 5 to about 8%, it was dumped from the vessel and allowed to cool below the softening point of the calcium salts. The mixture was then spread out in a thin layer and finely granulated. The resulting powder had a total fat content of about 70 to 72%, from 6 to 8% glycerol and 20 to 24% calcium. The product is analogous to the commercially available rumen protected fats that are calcium salts of long chained fatty acids.

Example 2

Ingredients: 380 grams white grease 100 grams CaO 100 grams water

The white grease, having a free fatty acid content from about 5 to about 15%, and CaO were mixed as in Example 1. Water was then mixed in to catalyze the reaction. The CaO was hydrolyzed and the total amount of free fatty acids were converted to their calcium salt form. The physical properties of the final product were similar to the product of Example 1.

Example 3

Ingredients: 100 grams yellow grease 15 grams CaO 15 grams water

The yellow grease was heated to 65° C., and the CaO was added and thoroughly mixed as the temperature increased to 90° C. The water was then added in small amounts and the material was stirred while the temperature rose to 120–150° C. After about 20 minutes, a taffy-like mass formed, was removed from the container, and was rolled, cooled and milled into dry free-flowing particles containing 82.3% crude fat and 0.6% moisture.

Example 4

Ingredients: 550 grams yellow grease 70 grams CaO 54 grams water

The ingredients were reacted as in Example 3. After 30 minutes, a dry, free-flowing material was obtained that was milled into small granules.

Example 5

Ingredients: 100 grams canola oil 100 grams sunflower oil 30 grams CaO 25 grams water The oils were heated to 65° C. The CaO was added and thoroughly mixed with the oils, with the temperature increasing to 90° C. The water was added, after which the temperature increased to 120° C. The mixture was slowly stirred until the temperature rose to 200° C., at which point the saponification reaction occurred, and the temperature dropped to 180° C. The material was removed from the reaction vessel and processed into a dry, free-flowing calcium soap that was milled into small granules.

Example 6

Ingredients: 100 grams canola oil 100 grams sunflower oil 30 grams CaO 30 grams water The procedure followed in Example 3 was repeated, except that the water was added after the temperature of the mixture of CaO and oils exceeded 110° C. The material saponified at 230° C., whereupon the temperature dropped to about 185° C., while a taffy-like material formed that was removed and processed into free-flowing calcium soap granules.

Example 7

Ingredients: 200 grams canola oil 30 grams CaO 30 grams water

The oil was heated to 65° C., after which the CaO was added and thoroughly mixed with the oil. The water was added at about 80° C. The mixture was stirred while the material boiled, during which time the temperature rose from 110° C. to 150° C. The stirring was then intermittent until the mixture again began a slow boil and the temperature rose to about 220° C. The material gave off a light smoke, then in about 1 minute it formed a yellow taffy-like material that was removed from the vessel and processed into a dry, free-flowing calcium soap that was milled into small granules. The total process took about 20 minutes.

Example 8

Ingredients: 200 grams sunflower oil 30 grams CaO 30 grams water

The ingredients were reacted as in Example 5, as were the ingredients for the following six examples:

Example 9

Ingredients: 200 grams soybean oil 30 grams CaO 30 grams water

Example 10

Ingredients: 200 grams olive oil 30 grams CaO 30 grams water

Example 11

Ingredients: 200 grams corn oil 30 grams CaO 30 grams water

Example 12

Ingredients: 200 grams tallow 30 grams CaO 30 grams water

Example 13

Ingredients: 200 grams lard 30 grams CaO 30 grams water

The present invention thus provides a process by which fatty acid calcium salt rumen bypass feed supplements in the form of a free-flowing granular material may be prepared in a single decomposition reaction from commercially available animal and vegetable fats and oils and fat byproducts of the food industry and restaurant trade. The foregoing examples and description of the preferred embodiment should be taken as illustrating, rather than as limiting, the present invention as defined by the claims. As will be readily appreciated, numerous variations and combinations of the features set forth above can be utilized without departing from the present invention as set forth in the claims. Such variations are not regarded as a departure from the spirit and scope of the invention, and all such modifications are intended to be included within the scope of the following claims.

What is claimed is:

1. A method for the preparation of a fatty acid calcium salt product comprising:

forming an admixture of reactive ingredients consisting of (a) a $C_{10}$–$C_{22}$ fatty acid mixture having greater than about 45 wt/% of the $C_{10}$–$C_{22}$ fatty acid content in the form of fatty acid glycerides; and (b) from about 10% to about 30% of the total admixture weight of calcium oxide;

Adding water to the admixture in an amount between about 10% and about 100% by weight relative to the weight of said calcium oxide; and Heating said admixture to a temperature between about 150° and 250° C., so that said fatty acid glycerides saponify to form fatty acid calcium salts.

2. The method of claim 1, further comprising the step of cooling said admixture and forming a solid, free-flowing and granular fatty acid calcium salt product.

3. The method of claim 1, wherein said $C_{10}$–$C_{22}$ fatty acid mixture has a glyceride content between about 85 and about 100 weight%.

4. The method of claim 1, wherein said $C_{10}$–$C_{22}$ fatty acid mixture is a fatty acid feedstock selected from the group consisting of yellow grease, white grease, lard, tallow, vegetable oils and fish oils.

5. The method of claim 1, wherein said admixture contains between about 15% and about 30% by weight of calcium oxide.

6. The method of claim 1, wherein said admixture comprises between about 10% and about 15% by weight of said calcium oxide.

7. The method of claim 6, wherein said temperature is between about 180 and about 220° C.

8. The method of claim 1, wherein said admixture further comprises a biologically active material.

9. The method of claim 8, wherein said biologically active material is an amino acid.

* * * * *